United States Patent [19]

Sluka et al.

[11] Patent Number: 5,416,001
[45] Date of Patent: May 16, 1995

[54] METHOD AND AGENT FOR THE DETECTION OF AN ANALYTE CONTAINING GLYCOSIDIC SURFACTANTS

[75] Inventors: Peter Sluka, Weilheim; Rainer Wehner, Tutzing, Germany

[73] Assignee: Boehringer Mannheim GmbH, Mannheim, Germany

[21] Appl. No.: 81,191

[22] Filed: Jun. 25, 1993

[30] Foreign Application Priority Data

Jun. 26, 1992 [DE] Germany .......................... 42 20 653.7

[51] Int. Cl.⁶ .................. G01N 33/545; G01N 33/546
[52] U.S. Cl. ....................................... 435/7.93; 435/6; 435/7.94; 435/7.95; 435/962; 436/531; 436/534; 436/826
[58] Field of Search ............... 435/962, 6, 7.93, 7.94, 435/7.95; 436/825, 826, 531, 534

[56] References Cited

U.S. PATENT DOCUMENTS 4,578,269 3/1986 Morein ................................. 424/89
4,900,549 2/1990 DeVries et al. ....................... 424/88
5,110,726 5/1992 Ogden ............................... 435/7.21

OTHER PUBLICATIONS

JAPIO Abstract of Japanesse Patent 01-245,159, issued Sep. 29, 1989, Y. Mizumura et al.
V. Chapman et al., J. Immunol. Methods, 149 (1992), 147-157.
M. Khristova et al., Acta Virol., 33 (1) (1989), 1-7.
R. Palfree et al., J. Immunol. Methods, 52 (1992), 395-408.
R. Peterson et al., Vision Research, 23 (3) (1983), 267-273.

*Primary Examiner*—Mary E. Ceperley
*Attorney, Agent, or Firm*—Nikaido, Marmelstein, Murray & Oram

[57] ABSTRACT

A method for detecting an analyte is disclosed in which the analyte is brought into contact with at least one receptor which is bound to or can be bound to a solid phase. In order to avoid unspecific interferences the addition of a glycosidic surfactant is proposed.

5 Claims, No Drawings

METHOD AND AGENT FOR THE DETECTION OF AN ANALYTE CONTAINING GLYCOSIDIC SURFACTANTS

The present invention concerns a method for the detection of an analyte in which the analyte is brought into contact with at least one specific receptor which is bound to or can be bound to a solid phase wherein a water-soluble glycosidic surfactant is added to the incubation medium and also concerns agents suitable therefor.

Methods are known for the detection of an analyte in a sample in which the analyte is brought into contact with a specific receptor which is bound to or can be bound to a solid phase. They are generally denoted heterogeneous methods. In the case of immunoassays different method variants are known e.g. the sandwich method, the indirect method and the competitive method.

In the sandwich method an antibody is bound to the carrier, the test solution is added whereupon the specific antigen present in the test solution is bound to the antibody. Then a labelled specific antibody for the antigen-antibody complex or for parts of this complex is added and binds to this complex. The amount of antigen can then be calculated via the labelled antibody.

In the indirect method an antigen is bound to the carrier material. Test solutions are added to this whereupon the antibody specific for the carrier-bound antigen which is present in the test solution reacts with the antigen. When a labelled antiglobulin is added, the antiglobulin binds to the antigen-antibody complex and the amount of unknown antibody in the test solution can be determined.

In the competitive method one of the partners of the immunoreaction is bound to the carrier material. A solution is then added which contains the other partner of the immunoreaction that is present in an unknown amount and also contains a known amount of the labelled other partner of the immunoreaction. Both partners, labelled and unlabelled, compete for the binding site of the partner of the immunoreaction bound to the carrier.

In all these method variants the receptor bound to the wall does not have to be bound directly to the solid phase. It is possible to use a second wall-bound receptor which specifically binds to the first receptor and binds it to the solid phase during the course of the test procedure whereby single or multistep test procedures are possible.

If the analyte is a nucleic acid the method is a hybridization test in which one receptor, in this case a nucleic acid which is complementary to the nucleic acid to be detected, is bound to or can be bound to the solid phase. Also in this case different method variants are known to a person skilled in the art.

All these known heterogeneous methods for detecting an analyte usually require additions of proteins, polysaccharides and/or surfactants which do not take part in the specific reaction but which favourably influence the result of the heterogeneous method. Heterogeneous methods are falsified to a variable extent by non-analyte specific interferences, so-called unspecific interferences which among experts are denoted "matrix effect", "background" or "unspecific binding".

Solid phase immunochemical tests were described in DE-A 36 38 767 to which lactoferrin, foetal calf serum and polyoxyethylene-20-sorbitan monolaurate (Tween ® 20) are added. When Tween ® 20 is added to the incubation medium at concentrations which are higher than 0.01%, the receptor bound to the carrier material can become detached which in turn leads to a negative influence on the detection method.

Thus non-ionic block copolymer surfactants with a HLB value of more than 20, such as Tetronic ®, were used in EP-A 0 215 457 in order to avoid unspecific interferences in immunological determinations in a heterogeneous phase. These surfactancts have the advantage that they do not lead to such a strong desorption of the wall-bound receptor compared to Tween ® 20. These block copolymer surfactants do not have a homogeneous composition but have a more or less broad distribution of homologues. The composition is subject to batch-dependent variation. Therefore in order to avoid unspecific interferences every batch has to be tested anew for its suitability in the respective detection method. As a result, in the past it turned out that some batches could not be used.

A further disadvantage of the surfactants which have usually been used is that toxic and cancerogenic starting materials such as for example ethylene oxide are used for their production. Surfactants of the ethylene oxide-propylene oxide block copolymer type are in addition difficult to degrade biologically.

The object was therefore to find a method for the detection of an analyte as well as an agent suitable therefor in which unspecific binding is prevented. The reagent necessary for this should not be subject to any or only to a negligible batch-dependent variation and it should be environmentally compatible.

This object was achieved by a method for the detection of an analyte in which the analyte is brought into contact with at least one specific receptor which is bound to or can be bound to a solid phase which is characterized in that a water-soluble glycosidic surfactant is added to the incubation medium.

Furthermore, the invention concerns an agent for detecting an analyte which contains at least one specific receptor which is bound to or can be bound to a solid phase and which also contains a water-soluble glycosidic surfactant.

Surface-active glycosidic surfactants have already been known for more than 50 years as raw materials for detergents, for example from the Austrian Patent 1 35 333 in which the production of lauryl glucoside is described. A method for producing alkylpolyglycosides (APGs) is described in DE-A 37 23 826. Such APGs are commercially available, for example under the trade name Plantaren ®. Synthesis of glycosidic surfactants is carried out by means of transglucosylation via an alkylglucoside. In the known syntheses of glycosidic surfactants exactly defined starting products can be used which lead to well defined products. Batch-dependent variations as observed in the case of block copolymers do not occur in this case to an extent which would interfere.

The defined glycosidic surfactants are also suitable such as for example octyl-D-glucopyranoside which can be produced by means of a more time-consuming synthesis according to Biochemistry 19, 4108–4115 (1980). In contrast to APGs which are mono-, di- and trisaccharides, these compounds represent real monosubstances.

According to the present invention glycosidic surfactants are understood in the following as reaction products from sugars and fatty alcohols whereby aldoses or ketoses such as glucose, fructose, mannose, galactose, xylose or ribose come into consideration as the sugar component. Glucose is particularly preferred.

Aliphatic as well as aromatic alcohols come into consideration as fatty alcohols. This fatty alcohol has to be selected so that the glycosidic surfactants are still readily water-soluble. Those aliphatic alcohols are preferably used whose alkyl residue has 4–18 carbon atoms, alkyl residues with 6–8 carbon atoms are particularly preferred.

Those aromatic alcohols are preferably used which have an aromatic ring on which, if desired, further groups which render them water-soluble are substituted such as —OH, —OCH$_3$ or —SO$_2$. Examples of aromatic alcohols are benzyl alcohol, salicyl alcohol and $\beta$-phenyl ethanol. Benzyl alcohol is particularly suitable. Hexylglucoside, octylglucoside and benzylglucoside or mixtures thereof have proven to be particularly suitable glycosidic surfactants.

Addition of these glycosidic surfactants suppresses unwanted reactions in methods for the detection of an analyte in which at least one specific receptor is bound to or can be bound to a solid phase and at the same time does not cause desorption of the specific receptor bound to the solid phase. Moreover glycosidic surfactants are not subject to extensive batch to batch variation so that comparable results are achieved from batch to batch.

All known analytes such as haptens, antigens, proteins, antibodies or nucleic acids can be detected using the heterogeneous method. The sample which contains the analyte to be detected can be for example blood, serum, plasma, secretions, liquor, urine or tissue products. The method is particularly suitable for detecting an analyte in plasma and serum since in this case results which correspond very well can be achieved. When the surfactants according to the present invention are not used strong undesired side reactions are very often observed in plasma so that the results can vary widely between plasma and serum samples.

The method according to the present invention can be used for all types of plasma. It can be used for plasma to which EDTA has been added for stabilization as well as for plasma to which heparin or citrate has been added.

The method can be carried out as a competitive, indirect or sandwich method. Depending on the method variant the specific receptor is understood as a hapten or antigen as in the case of the competitive or indirect method, an antibody or a fragment thereof as in the case of a sandwich method or a nucleic acid or a nucleic acid fragment as in the case of a hybridization test.

In this connection the specific receptor can be bound directly to the solid phase or can be bound to the solid phase during the procedure. If the specific receptor is only bound during the procedure, it then preferably consists of a conjugate of a specific receptor such as an antigen, antibody or a nucleic acid and a substance S1. A substance S2 which is capable of specific binding to the substance S1 is then bound to the solid phase. Antigen-antibody, hapten-antibody, biotin-avidin or streptavidin, protein-antiprotein, protein A-immunoglobulin, haemoglobin-haptoglobin or enzyme-substrate are particularly suitable as specifically bindable substance pairs S1-S2. Biotin is preferably used as S1 and streptavidin or avidin as S2.

A water-insoluble carrier to which one or several specific receptors are bound or can be bound is to be used as the solid phase within the meaning of the invention.

Solid phases are for example latex particles, beads, tubes and microtitre plates made of various plastic materials such as for example polystyrene and also absorptive or porous materials. Such solid phases are known to a person skilled in the art.

The type and method of labelling which is finally used to detect the complex of specific receptor and analyte bound to the solid phase is known to a person skilled in the art.

All the usual labelling agents such as radioactive labels, enzymes, fluorescent or chemiluminescent substances can be used.

The water-soluble glycosidic surfactants can be added to any of the solutions used for the determination. The glycosidic surfactants can also even be added when preparing the sample for the test. The surfactants are preferably added to the reaction buffer or correspondingly to the reaction buffers in a two-step or multistep procedure. The buffers can in addition contain stabilizing additives such as proteins or polysaccharides, preservatives and other usual additives apart from the buffer substances and the specific receptors which may be present therein.

The water-soluble glycosidic surfactants are used in an amount of 0.1 to 2% in relation to the weight of the total reaction preparation. A concentration of 0.5 to 1.0% is preferred.

An agent is used to carry out the method which contains a specific receptor which is bound to or can be bound to a solid phase and which is characterized in that it contains a water-soluble glycosidic surfactant. This agent can in addition contain other common constituents.

Buffers, proteins such as bovine serum albumin or IgG and/or preservatives can for example be present. In addition it also contains a conjugate of a label and a specific receptor or in the case of a competitive test a conjugate of a label and an analyte or analyte analogue. If an enzyme is used as the label the agent in addition contains a system for the detection of the enzymatic activity.

The agent preferably contains APGs based on hexylglucoside, octylglucoside or benzylglucoside or mixtures thereof or analogous defined monosubstances as glycosidic surfactants. The glycosidic surfactants are present in the agent at a concentration of 0.1–2% in relation to the weight of the total reaction preparation.

Using the method and agent according to the present invention it is possible to improve the recovery in analyte determinations in a heterogeneous phase. In addition undesired side reactions are suppressed, such as in particular the unspecific attachment of conjugates to the solid phase, without increasing the detachment of the bound reaction partners. Problems which occur when using samples which exhibit undesired side reactions, in particular plasma samples, are eliminated. Variations between different batches are minimized by the defined and more homogeneous composition of the APGs and by the defined composition of the glycosidic surfactants produced according to Biochemistry 19 (1980), 4108–4115. A further positive effect is that the environmental compatibility of the glycosidic surfactants is good to very good.

The invention is elucidated by the following examples:

EXAMPLE 1

Production of hexyl glucopyranoside 400 g 1-hexanol is distilled together with 3.6 g p-toluene sulfonic acid in a 2 l multinecked flask with stirrer and distillation attachment and heated to 110° C. Then a suspension of 300 g anhydrous glucose in 300 g 1-hexanol is added to the preparation in portions and namely in four portions. After the first portion has been added a vacuum (300 mbar) is applied and the reaction water which forms is rapidly distilled off. As soon as it has all dissolved the next portion is added. The other portions are treated accordingly. After addition of the last portion, as soon as only hexanol distils over the preparation is aerated and adjusted to pH 8 with sodium ethylate. Subsequently the hexanol is distilled off at 80° C. in a high vacuum. The oily residue is dissolved in 7 l water and extracted twice with 1 l ethyl acetate in each case. The aqueous phase is evaporated and subsequently lyophilized. 275 g of a faintly yellow coloured substance is obtained.

EXAMPLE 2

Production of benzyl glucopyranoside 800 g benzyl alcohol and 3.6 g p-toluene sulfonic acid are placed in a 3 l multinecked flask with stirrer and distillation attachment and heated to 110° C. Then a suspension of 300 g anhydrous glucose in 500 g benzyl alcohol is added to the preparation in portions and namely in four portions. After the first portion has been added a vacuum is applied and the reaction water which forms is rapidly distilled off. Each of the next portions are added when the glucose has clearly dissolved. After addition of the last portion, as soon as only benzyl alcohol distils over the preparation is aerated and the catalyzer is neutralized with sodium ethylate. Subsequently the benzyl alcohol is distilled off at 80° C. in a high vacuum. The oily residue is dissolved in 2 l water. After 8 hours the excess benzyl alcohol separates at the bottom of the vessel. The aqueous phase is decanted off and extracted once with 400 ml ethyl acetate. The aqueous phase is concentrated further and subsequently lyophilized. 360 g of a faintly yellow coloured solid substance is obtained.

EXAMPLE 3

The influence of various detergents on the shape of the calibration curve was determined using the Enzymun test ® LH from Boehringer Mannheim GmbH as an example. The test for the detection of luteinizing hormone (LH) was carried out according to the manufacturer's instructions.

Tween ® 20 or hexylglucoside or benzyl glucopyranoside at concentrations between 0.005 and 1% was added to the incubation buffer (40 mmol/l phosphate buffer pH 7.4)

Table 1 shows the influence of Tween ® 20 on the shape of the calibration curve for the Enzymun test ® LH. At a Tween ® 20 concentration of 0.5% the slope of the calibration curve is 60-70% less than the calibration curve without addition of detergent.

Table 2 shows the influence of the addition according to the present invention of the glycosidic detergents hexylglucoside and benzyl glucopyranoside on the shape of the calibration curve. When 0.5% detergent is added the slope of the calibration curve is only decreased by 5-10% compared to the control without addition of detergent.

TABLE 1

Enzymun test ® LH
Influence of Tweene ® 20 on the shape of the calibration curve
The absorbance was measured at 405 nm in mA. The standards a–f (LH in a bovine serum matrix) of the Enzymun test ® LH served as the sample.

| | Concentration of Tween ® 20 in % | | | |
|---|---|---|---|---|
| | 0 | 0.005 | 0.05 | 0.5 |
| Standard a (mA) | 29 | 21 | 20 | 23 |
| Standard b (mA) | 68 | 56 | 41 | 38 |
| Standard c (mA) | 208 | 167 | 111 | 85 |
| Standard d (mA) | 491 | 386 | 272 | 165 |
| Standard e (mA) | 1208 | 982 | 665 | 405 |
| Standard f (mA) | 2117 | 1677 | 1198 | 766 |

TABLE 2

Enzymun test ® LH
Influence of glycosidic detergents on the shape of the calibration curve
The absorbance was measured at 405 nm

| | Concentration (%) | Standard a (mA) | Standard f (mA) |
|---|---|---|---|
| without detergents | — | 25 | 2045 |
| hexylglucoside | 0.1 | 21 | 1986 |
| hexylglucoside | 0.5 | 13 | 1837 |
| hexylglucoside | 1 | 12 | 1615 |
| benzyl glucopyranoside | 0.1 | 18 | 1979 |
| benzyl glucopyranoside | 0.5 | 19 | 1930 |
| benzyl glucopyranoside | 1 | 15 | 1785 |

TABLE 2

Enzymun test ® LH
Influence of glycosidic detergents on the shape of the calibration curve
The absorbance was measured at 405 nm

| | Concentration (%) | Standard a (mA) | Standard f (mA) |
|---|---|---|---|
| without detergents | — | 25 | 2045 |
| hexylglucoside | 0.1 | 21 | 1986 |
| hexylglucoside | 0.5 | 13 | 1837 |
| hexylglucoside | 1 | 12 | 1615 |
| benzyl glucopyranoside | 0.1 | 18 | 1979 |
| benzyl glucopyranoside | 0.5 | 19 | 1930 |
| benzyl glucopyranoside | 1 | 15 | 1785 |

EXAMPLE 4

The influence of various batches of detergents on the shape of the calibration curve and recovery in human serum was determined using the Enzymun test ® LH as an example. Various Pluronic F68 batches were used as the state of the art method and the results obtained were compared with various batches of benzylglucoside. The detergents were added to the incubation buffer of the Enzymun test ® LH at a concentration of 0.5% as in the previous examples. The recovery was tested on various human sera.

Calibration curves were established with the respective batches using standards a–f. The respective LH concentration was read from the absorbances of the human serum samples using the calibration curve.

It can be seen from Table 3 that the calibration curves differ significantly depending on the Pluronic F68 batch used. On average the recovery in human sera differs in these batches by up to 16%.

It can be seen from Table 4 that the calibration curves do not differ significantly when using different batches of benzylglucoside. When using these batches the recovery only differs by 4%.

TABLE 3

Enzymun test ® LH
Batch dependence of Pluronic F68
Influence on the shape of the calibration curve and recovery in human sera

| Pluronic F68 batch | A | % RE | B | % RE | C | % RE |
|---|---|---|---|---|---|---|
| a) Calibration curves | | | | | | |
| Standard a (mA) | 21 | | 17 | | 19 | |
| Standard b (mA) | 49 | | 44 | | 52 | |
| Standard c (mA) | 169 | | 138 | | 176 | |
| Standard d (mA) | 411 | | 341 | | 434 | |
| Standard e (mA) | 1070 | | 883 | | 1116 | |
| Standard f (mA) | 1832 | | 1536 | | 1925 | |
| b) Recovery (RE) in human sera (HS) | | | | | | |
| HS 1 (mIU/ml) | 15.9 | 100 | 17.2 | 108 | 14.7 | 92 |
| HS 2 (mIU/ml) | 8.8 | 100 | 9.1 | 103 | 7.5 | 85 |
| HS 3 (mIU/ml) | 9.1 | 100 | 9.4 | 103 | 7.9 | 87 |
| HS 4 (mIU/ml) | 6.3 | 100 | 6.9 | 110 | 5.5 | 87 |
| HS 5 (mIU/ml) | 64.2 | 100 | 74.9 | 117 | 65.0 | 101 |
| HS 6 (mIU/ml) | 48.7 | 100 | 56.0 | 115 | 48.7 | 100 |
| HS 7 (mIU/ml) | 48.1 | 100 | 51.5 | 107 | 43.7 | 91 |
| HS 8 (mIU/ml) | 35.5 | 100 | 39.2 | 110 | 34.2 | 96 |
| average recovery in % | | 100 | | 109 | | 93 |

TABLE 4

Enzymun test ® LH
Influence of various batches of benzylglucoside on the shape of the calibration curves and on the recovery in human sera

| Benzylglucoside batch | A | % RE | B | % RE | C | % RE |
|---|---|---|---|---|---|---|
| a) Calibration curves | | | | | | |
| Standard a (mA) | 34 | | 33 | | 32 | |
| Standard b (mA) | 68 | | 68 | | 65 | |
| Standard c (mA) | 217 | | 220 | | 202 | |
| Standard d (mA) | 458 | | 466 | | 434 | |
| Standard e (mA) | 1166 | | 1176 | | 1131 | |
| Standard f (mA) | 2012 | | 2004 | | 1915 | |
| b) Recovery (RE) in human sera (HS) | | | | | | |
| HS 1 (mIU/ml) | 4.7 | 100 | 4.7 | 100 | 4.7 | 100 |
| HS 2 (mIU/ml) | 16.3 | 100 | 15.6 | 96 | 16.2 | 99 |
| HS 3 (mIU/ml) | 4.4 | 100 | 4.5 | 102 | 4.8 | 109 |
| HS 4 (mIU/ml) | 26.7 | 100 | 26.5 | 99 | 27.9 | 104 |
| average recovery in % | | 100 | | 99 | | 103 |

The following documents are incorporated by reference in this specification for their disclosure of certain glycosidic surfactants and methods of producing same: German patent DE-A 37 23 826; Austrian patent AT 1 35 333; and Biochemistry, Vol. 19, pp. 4108–4115 (1980).

We claim:

1. In a heterogeneous method for the detection of an analyte in a sample, comprising incubating the analyte in a medium with at least one specific receptor which receptor is bound directly or indirectly to a solid phase; the improvement which comprises providing a sufficient amount of a water soluble glycosidic surfactant in said reaction medium to suppress non-analyte specific interferences with said solid phase wherein the surfactant is used at a concentration of 0.1 to 2% based on the weight of the total reaction mixture.

2. The method of claim 1, wherein the water-soluble glycosidic surfactant is at least one selected from the group consisting of hexylglucoside, octylglucoside, benzylglucoside, and alkylpolyglycosides based on hexylglucoside, octylglucoside or benzylglucoside.

3. The method of claim 1, wherein the analyte to be detected is contained in a plasma sample.

4. The method of claim 1, wherein said heterogeneous method is a competitive, indirect or sandwich method or a hybridization test.

5. The method of claim 1, wherein said solid phase is a latex particle, a bead, a tube or a microtiter plate.

* * * * *